United States Patent [19]

Ragland

[11] Patent Number: 5,471,542
[45] Date of Patent: Nov. 28, 1995

[54] POINT-OF-GAZE TRACKER

[76] Inventor: Richard R. Ragland, 2010 Sea Village Cir., Cardiff, Calif. 92007

[21] Appl. No.: 126,892

[22] Filed: Sep. 27, 1993

[51] Int. Cl.⁶ .................................................. G06K 9/00
[52] U.S. Cl. ............................................ 382/128; 351/208
[58] Field of Search ............................... 382/1, 6, 2, 48; 351/200, 206, 208, 210

[56] References Cited

U.S. PATENT DOCUMENTS

| | | | |
|---|---|---|---|
| 3,986,030 | 10/1976 | Teltscher | 250/349 |
| 4,109,237 | 8/1978 | Hill | 380/2 |
| 4,568,159 | 2/1986 | Baldwin | 351/210 |
| 4,613,219 | 9/1986 | Vogel | 351/209 |
| 4,620,318 | 10/1986 | Hill | 351/208 |
| 4,641,349 | 2/1987 | Flom et al. | 351/206 |
| 4,648,052 | 3/1987 | Friedman et al. | 364/550 |
| 4,720,189 | 1/1988 | Heynen et al. | 351/210 |
| 4,768,088 | 8/1988 | Ando | 358/93 |
| 4,789,235 | 12/1988 | Boran et al. | 351/246 |
| 4,859,050 | 8/1989 | Boron et al. | 351/210 |
| 4,946,271 | 8/1990 | Palsgard et al. | 351/210 |
| 4,950,069 | 8/1990 | Hutchinson | 351/210 |
| 4,973,149 | 11/1990 | Hutchinson | 351/210 |
| 4,975,969 | 12/1990 | Tal | 382/2 |
| 5,016,282 | 5/1991 | Tomono et al. | 382/2 |
| 5,291,560 | 3/1994 | Daugman | 382/6 |
| 5,293,427 | 3/1994 | Ueno et al. | 382/6 |

*Primary Examiner*—Joseph Mancuso
*Attorney, Agent, or Firm*—Calif Kip Tervo

[57] ABSTRACT

The tracker determines a vision vector for an eye of an operator. The device generally comprises: a video camera oriented so as to observe an eye of an operator for obtaining an image of the eye; camera interface electronics and image processor for digitizing the image of the operator's eye and for analyzing the digitized image for determining therefrom a plurality of points determinative of the iridal ellipse, the points being on the boundary between the eye's sclera and iris as represented by different light intensities; and a processor for utilizing said information and an estimate of the diameter of the iris in formulating an estimated optical axis vector for the eye. If the position and orientation of the camera is known relative to the operator's eye, then the pupillary ellipse can be used instead of the iridal ellipse. The tracker of the invention can be used as a mouse emulator attached to a mouse port of a personal computer system.

17 Claims, 7 Drawing Sheets

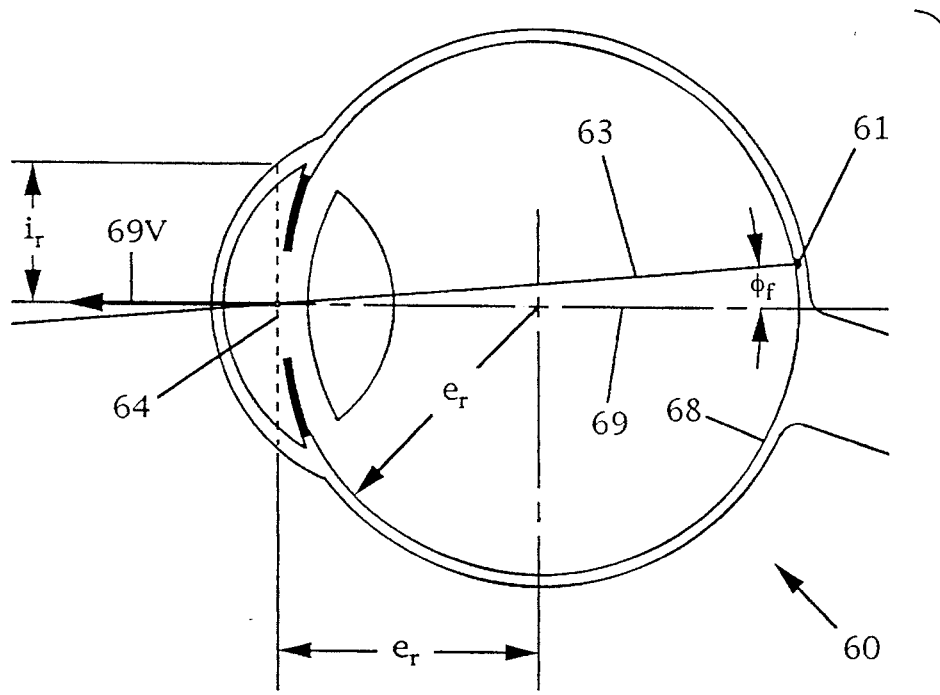
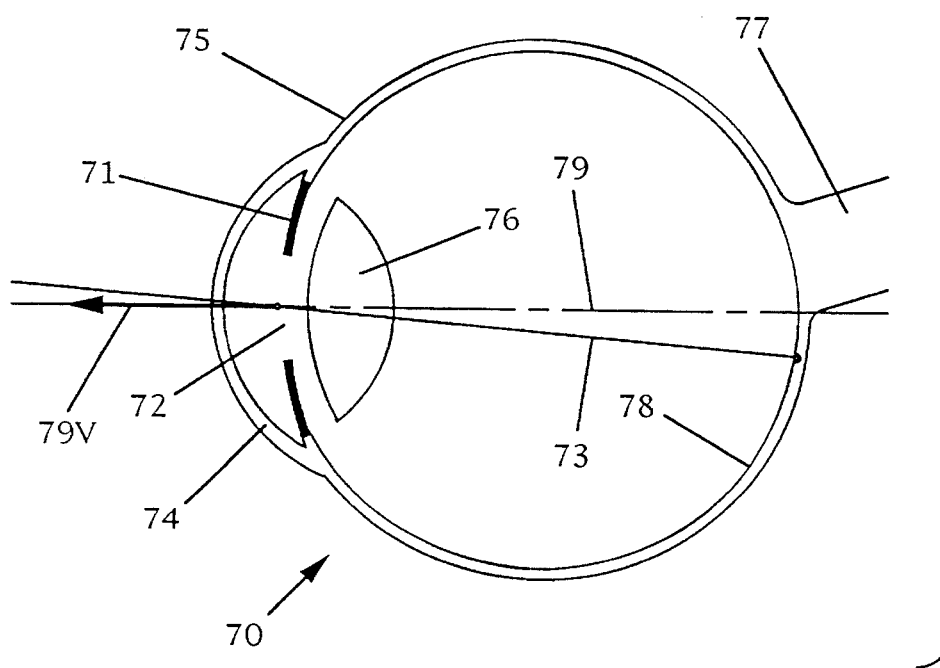
Fig. 4

POINT-OF-GAZE TRACKER

BACKGROUND OF THE INVENTION

1. Field of the Invention

This invention relates in general to a device and method for determining where a person is looking and more specifically involves analysis of a digitized image of the person's eye to determine the location and orientation of the iris or pupil in the image to determine an optical axis vector for that eye.

2. Description of the Related Art

The majority of patents in this area describe computer input devices for users who are physically handicapped. Most of these devices are based upon use of an infrared-sensitive image sensor and a collimated infrared source. The position of the subject's pupil (in the sensor's image frame) with respect to a corneal "glint" provides an estimate of the visual axis for one of the subject's eyes. An initial calibration procedure, during which the subject is asked to fix his gaze upon certain "known" points, reduces the error estimate to an acceptable level for subsequent operation.

Another technique initially maps surface veins on the retina (of one of the subject's eyes) through the pupillary opening and then tracks those portions of the map revealed through the pupil as the subject looks around.

Other methodologies depicted in the art are less practical than these and range from the merely cumbersome to the highly improbable. Regardless, none of the prior art methods is particularly precise or reliable.

This patent describes a point-of-gaze tracker which achieves improved precision and reliability by tracking the optical axes of both eyes in a novel way.

SUMMARY OF THE INVENTION

A person's point of gaze is the point in the surrounding space that is the instantaneous object of the person's visual regard. A point-of-gaze tracker determines a vision vector for an eye of an operator. The device generally comprises: a video camera oriented so as to observe an eye of an operator for obtaining an image of the eye; camera interface electronics and image processor for digitizing the image of the operator's eye and for analyzing the digitized image for determining therefrom a plurality of points determinative of the iridal ellipse, the points being on the boundary between the eye's sclera and iris as represented by different light intensities; and a processor for utilizing said information and an estimate of the diameter of the iris in formulating an estimated optical axis vector for the eye. If the position and orientation of the camera is known relative to the operator's eye, then the pupillary ellipse can be used instead of the iridal ellipse.

The point-of-gaze tracker of the invention can be used as a mouse emulator attached to a mouse port of a personal computer.

Other features and many attendant advantages of the invention will become more apparent upon a reading of the following detailed description together with the drawings in which like reference numerals refer to like parts throughout.

BRIEF DESCRIPTION OF THE DRAWINGS

FIG. 4 is a schematic model of human eyes viewed from the top in cross-section.

FIG. 7a is a diagram of an eye in the virtual image plane. A Z axis is included to provide a point of reference to FIG. 7b.

FIG. 7b depicts the point-of-gaze XYZ coordinate system which includes the image plane depicted in FIG. 7a.

DETAILED DESCRIPTION OF A PREFERRED EMBODIMENT

Figure 1:
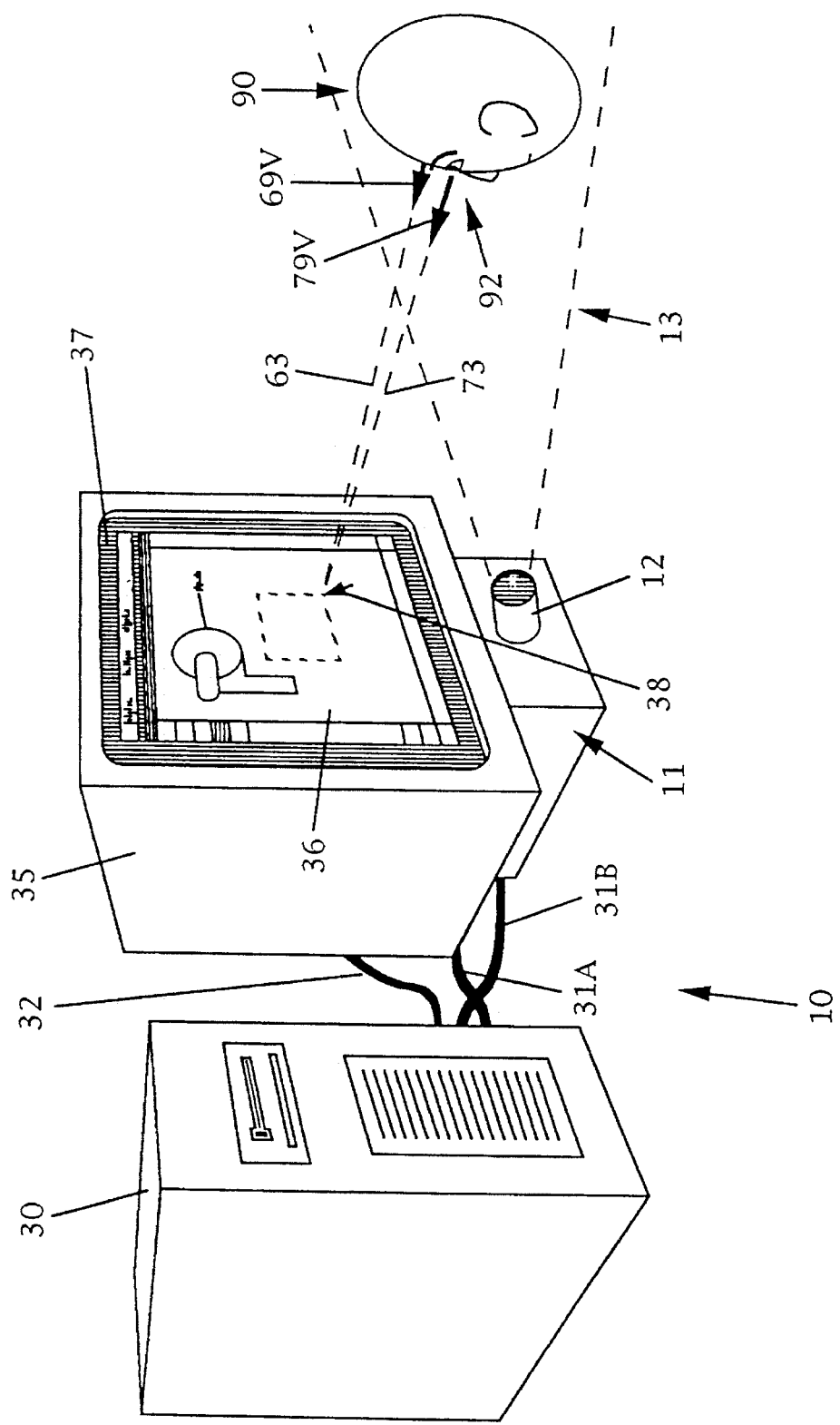
FIG. 1 is a perspective drawing of an exemplary point-of-gaze tracking system as embodied in a mouse emulator for a personal computer.

With reference now to the drawings, and more particularly to FIG. 1 thereof, there is shown a perspective drawing of a personal computer system, denoted generally as 10, where the standard computer mouse input device has been replaced by he preferred embodiment of the present invention, a mouse emulator, denoted generally as 11. Mouse emulator 11 is physically attached to personal computer monitor 35. The emulator enclosure contains within it a CCD (charge coupled device) array, an image processor, control processor, memory and camera control electronics. A video camera lens cylinder 12 is shown protruding from the emulator enclosure. Computer 30 is connected, such as by cable 32, to monitor 35. The CCD array, through camera lens 12 with field-of-view 13 shown bounded by dashed lines, obtains an image of operator 90. Camera lens cylinder 12 is oriented so as to provide images of the eyes, denoted generally as 92, of operator 90. Preferably, the position and orientation of the emulator's optical system is physically fixed relative to monitor 35 in order to maintain geometric references between the calculated point-of-gaze and monitor 35.

Monitor screen 37 may present to the operator the output of any standard software package running on the computer, such as the drawing environment 36 shown. Operator 90 manipulates graphical objects in the environment by causing his gaze to move mouse cursor 38 around the screen 37 in much the same way another operator would when using a manual computer mouse.

As will be further explained, emulator 11 permits the operator's eyes 92 to function as a computer mouse. In other words, emulator 11, in conjunction with the operator's eyes, emulates a mouse. Operator 90 may operate personal computer 30 by means of his gaze upon monitor screen 37. Dashed lines 63 and 73 represent the operator's visual axes, for the left and right eyes, respectively. At the instant shown, the operator's eyes 92 are focused on and are manipulating mouse cursor 38 on monitor screen 37 in order to operate a drawing tool in a standard software drawing environment 36 running on computer 30.

Figure 2:
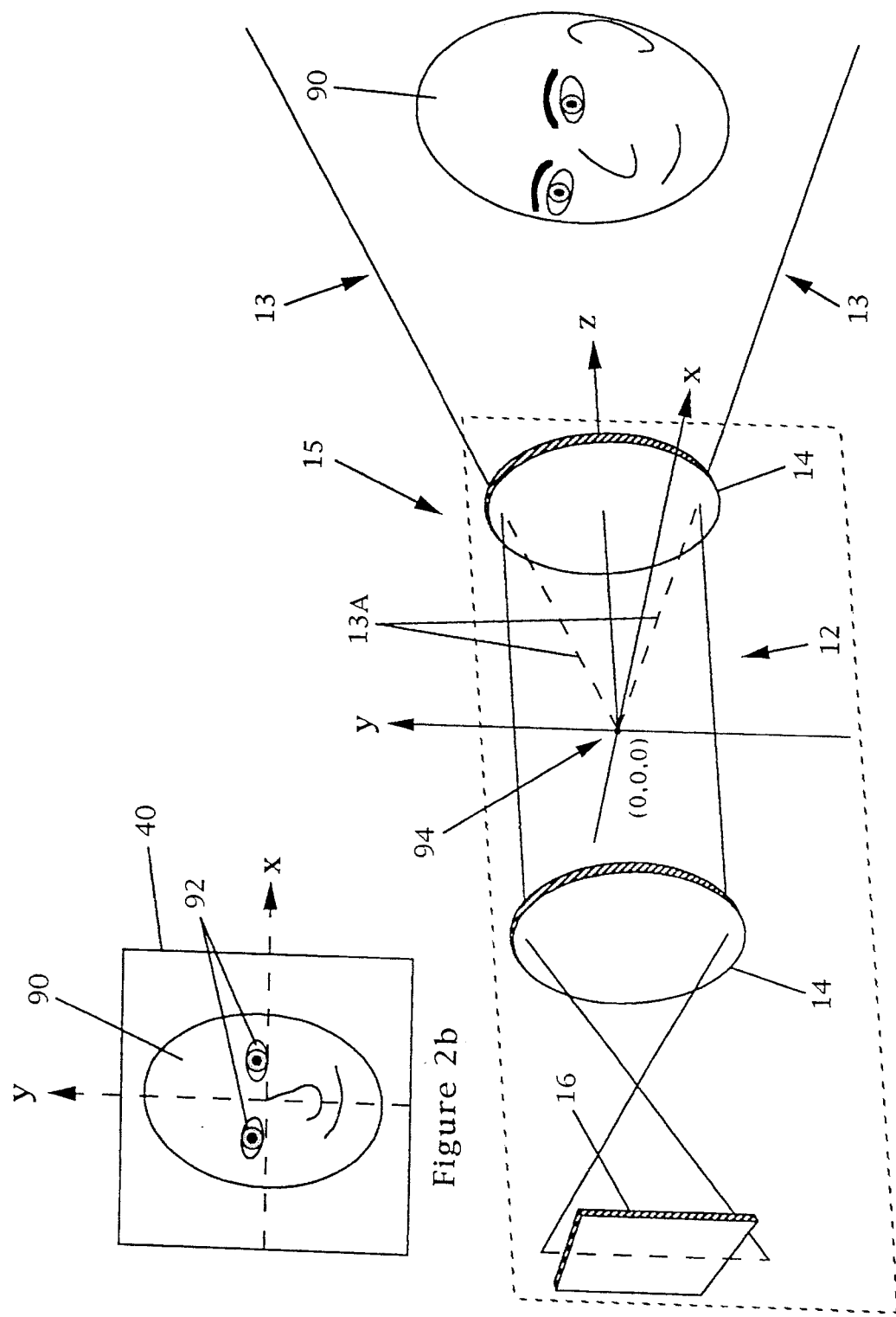
FIG. 2a is a diagram of the emulator's image sensor optics and the spatial reference axes of the system of FIG. 1.
FIG. 2b is a diagram of the virtual image plane.

FIGS. 2a and 2b illustrate the physical relationships between operator 90 and the lenses which form a part of video camera 15 in an XYZ coordinate system 94 providing the physical frame of reference needed for the point-of-gaze methodology as described herein. The camera's optical lenses 14 transmit the image, bounded by field-of-view 13, to a CCD array 16. If light rays representing the limits of the field-of-view 13 are extended inside lens cylinder 12 (along dashed lines 13A), they will meet in point (0,0,0), the origin of the stated point-of-gaze coordinate system. The x and y axes of this system are parallel to the plane of CCD sensor 16, and the z axis is, of course, orthogonal to that plane.

Images of the three-dimensional world outside the camera, as collected by CCD array 16, may be considered as a projection of that world upon a virtual image plane, representatively shown as 40 in FIG. 2b. Inside the electronics of emulator 11, this image plane 40 is represented by an array of digitized pixel (picture element) gray-scale values stored in memory. The pixel values in that array can be organized most effectively when the virtual image plane they represent is bisected by x and y axes as shown, with one quarter of the pixel values located in each quadrant. Further, for the purposes of this point-of-gaze methodology, the virtual image plane described may be considered as occupying a particular position in physical space: i.e., where the x and y axes of the image plane exactly coincide with the x and y axes of the XYZ coordinate system 94. In consequence, the physical relationships between all elements shown in FIG. 2a are well defined: emulator 11 and, by extension, video camera 15 are physically attached to that scene which is the object of the operator's visual regard (e.g. the computer's monitor screen 37 in the preferred embodiment); the XYZ coordinate system is physically defined by the video camera's optical system; and the virtual image plane 40 is, for technical convenience, placed in a position coincident with the spatial xy plane in the XYZ coordinate system.

Figure 3:
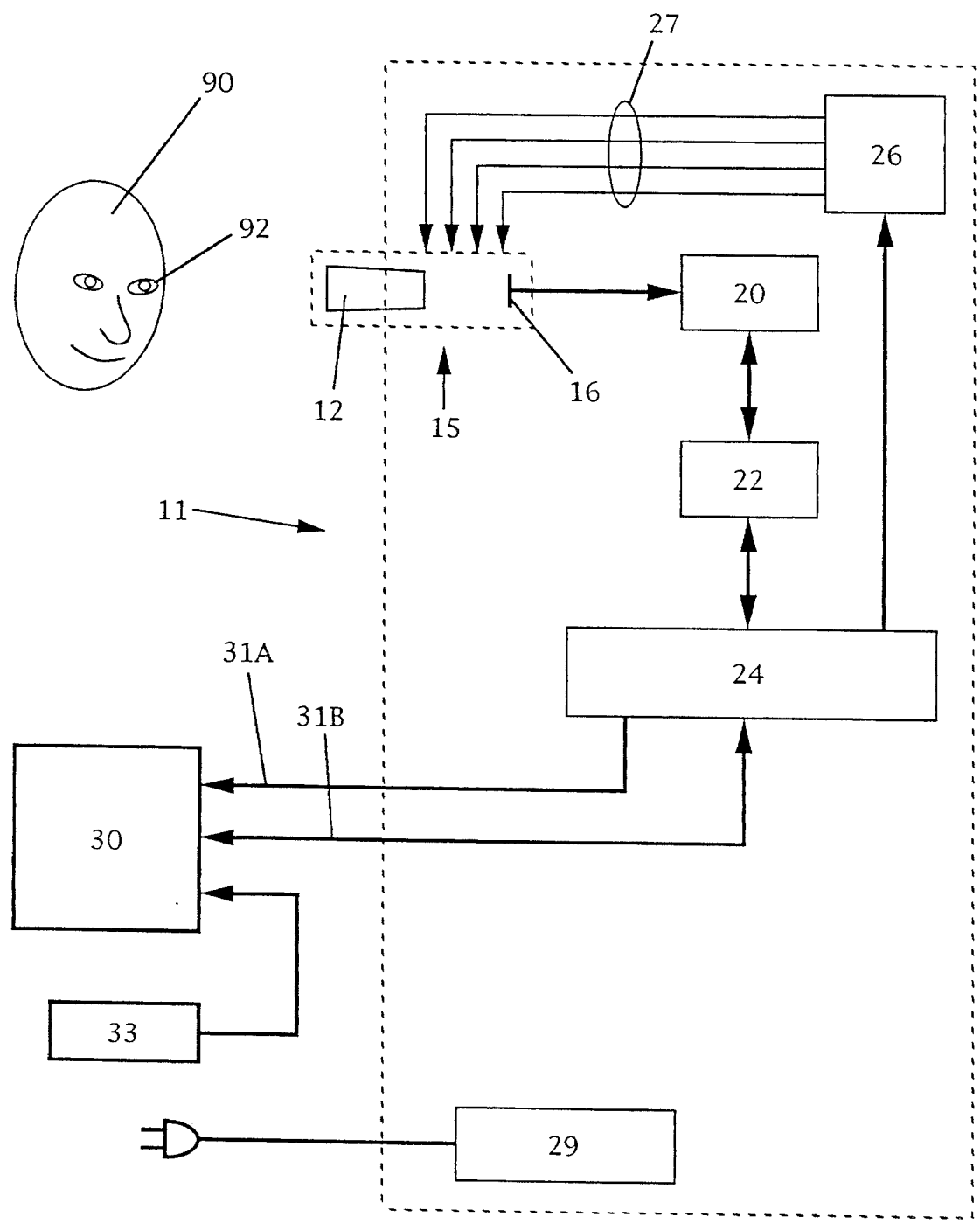
FIG. 3 is a block diagram depicting functional segmentation within the mouse emulator of FIG. 1 as well as external connections to the personal computer.

FIG. 3 is a block diagram depicting functional segmentation within mouse emulator 11 as well as external connections to the personal computer 30. Inside emulator 11, camera 15 provides images to an image processor 20 in the form of pixel arrays. Image array size is dependent on the array size of CCD sensor 16.

A CCD sensor needed to collect images for the point-of-gaze methodology described herein conceivably could range in size from a few hundred pixels square to one or two thousand on a side, depending on physical constraints and the resolution required for a particular application. In this case, for a mouse emulator configured as shown, one of the larger CCD arrays will provide enough resolution over a relatively wide field of view that operator 90 will be able to move his head—in and out, back and forth, as comfort or inclination requires—to a degree well beyond the operational capabilities of current gaze-tracking devices.

When exposed to light entering camera 15 through lens 12, each pixel in CCD array 16 accumulates an electric charge which is proportional to the intensity of the light incident upon that pixel. Each pixel's charge is gated (at a rate appropriate to the needs of the application) through an analog circuit which converts it to a voltage. The resultant voltage is proportional to the gray-scale value assigned to the intensity of the light falling upon that pixel. This series of gated pixel voltages is then sampled digitally and stored in memory 22 by image processor 20. The gray-scale assigned to a particular intensity level is not absolute; it depends directly upon the range of gray-scales and light intensities allowed by the system. Preliminary study indicates an 8-bit value (256 gray-scales) may be the best match for the preferred embodiment.

Successive images are operated on by image processor 20, where standard image processing techniques well known in the art, such as filtering, thresholding, edge detection, segmentation, and pattern recognition help locate the operator's eyes within each image. The control processor 24 then implements algorithms, hereinafter defined, which, from the location and orientation of the irises (or pupils) of the operator's eyes 92 in image plane 40, mathematically determine the location and orientation of the operator's optical axes in an attendant XYZ coordinate system. Subsequent calculations determine the output needed to place the mouse cursor at the operator's point-of-gaze (as shown in FIG. 1). This output is then transmitted to the computer over cable 31A to the computer mouse connection port in emulation of the computer's mouse. The SCSI connection 31B between control processor 24 in emulator 11 and personal computer 30 provides an interface to the emulator control software running on the computer which coordinates initialization procedures and keystroke entry as mediated by the operator's point-of-gaze. Most of the emulator's processing and interface electronics could certainly be implemented on a circuit board manufactured to reside in one of the computer's expansion slots, thus circumventing the need for a hardwired mouse input and SCSI connection, but the preferred embodiment depicts a more or less universal device which can be manufactured to operate with a variety of computers already in use.

Emulator 11 could also, in conjunction with other software packages running on computer 30, emulate mouse operation for the purposes of entering and editing text in a word processing environment, or to perform any other function in the repertoire of a standard computer mouse. Computer 30 is shown also connected to a keyboard 33 as an alternative input device.

Emulator 11 also includes a power supply and distribution network, shown symbolically as 29, for distributing power to the components. Camera 15 is physically controlled over control lines 27 by camera control interface 26 which receives input from control processor 24. Camera control functions may include iris, focus, tilt and zoom.

Model of the Human Eye

FIG. 4 schematically illustrates cross-sections of a model of two human eyes, denoted generally as 60 and 70, developed specifically for the algorithms employed by the methodology described herein. The model is primarily based upon Gullstrand's schematic eye, supplemented by generic physiological data. A few details are new, however, resulting from requirements unique to this point-of-gaze method. All of the components depicted in both cross-sections may be considered as lying in a single plane, as though a slice had been taken through an upright human head through the center of both eyes to reveal the details shown. Models shown for the right 60 and left 70 eyes are mirror images of one another.

The illustration representing left eye 70 shows the physiology of the human eye. The lens 76 is located just behind the iris 71 and opening of pupil 72. All are protected by the cornea 74. The sclera 75, or "white" of the eye, covers the eyeball from the edge of cornea 74 around to the optic nerve 77. Light entering pupil 72 is gathered by the retina 78, which acts something like a CCD sensor in a video camera, sending images through optic nerve 77 to the appropriate processors inside the human brain. Vision related axes include optical axis 79 and visual axis 73.

The illustration representing the right eye 60 shows the physical relationships between the optical axis 69, the visual axis 63, and the apparent disc of the iris 64 (as magnified slightly by the cornea). The fovea 61 is an area of retina 68 where the retina's light gathering sensors are concentrated for increased resolution. As stated before, in this model, for the purposes of the point-of-gaze algorithms, all four axes, i.e. the optical 69,79 and visual 63,73 axes of both eyes, lie in the same plane. Additionally, as shown in the illustration of the right eye 60, optical axis 69 and visual axis 63 intersect at the center of the apparent iridal disc 64. Optical axis 69 is orthogonal to apparent iridal disc 64, while visual axis 63 extends from the fovea 61 through the center of disc 64 to the object being viewed. In this illustration, $\phi_f$, the angle between the optical and visual axes, $i_r$, the radius of the apparent iridal disc, and $e_r$, the internal radius of the eyeball, represent values which differ slightly from individual to individual and will thus be defined as variables for the discussion which follows.

Detailed Description of the Critical Algorithms

Figure 5:
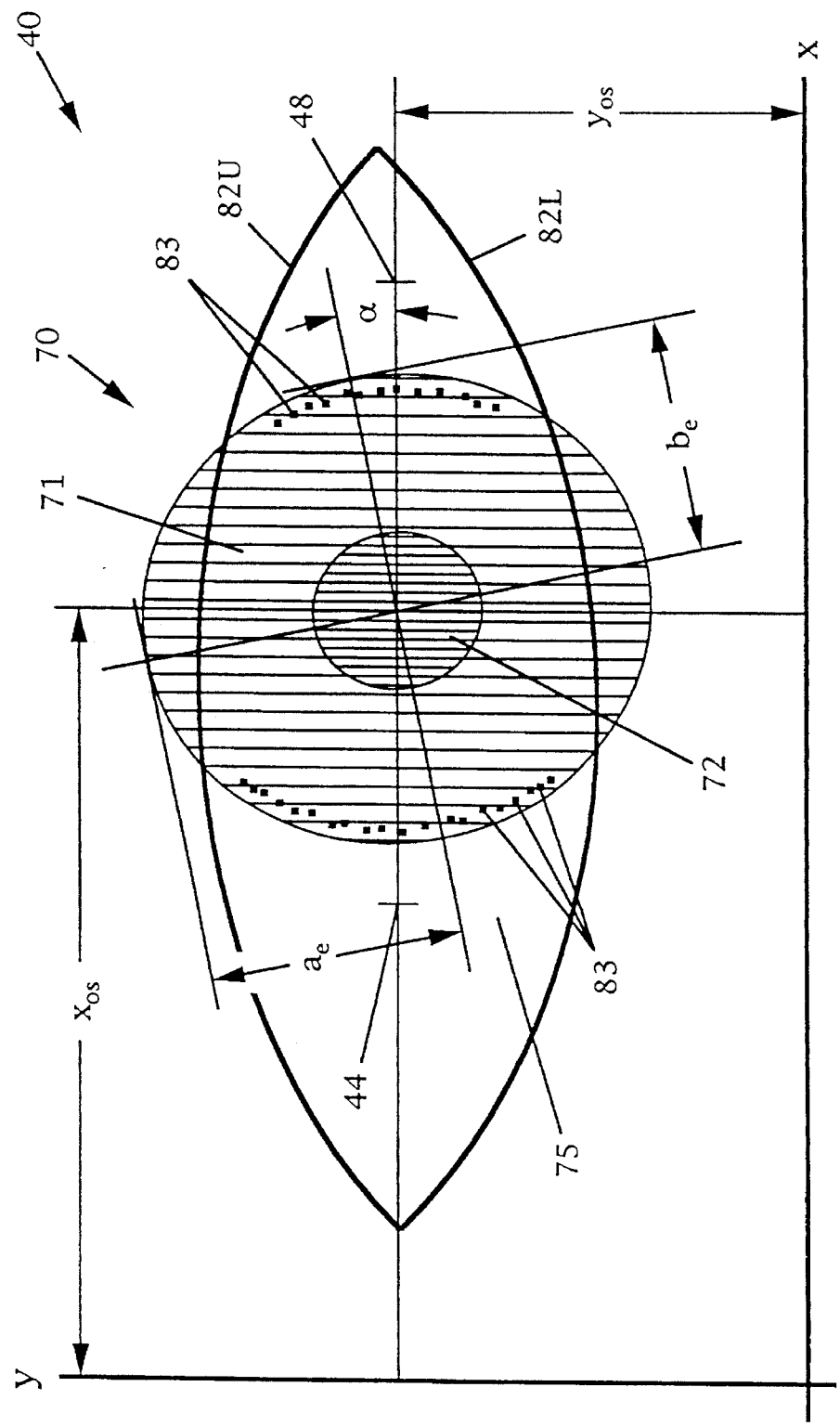
FIG. 5 is a diagrammatic view of an image of the operator's left eye in the first quadrant of the virtual image plane.

FIG. 5 is a diagrammatic view of, among other things, what an image captured by emulator 11 might look like, with the operator's left eye 70 shown in the first quadrant of virtual image plane 40. Eye 70 is seen between upper eye lid 82U and lower eye lid 82L. Sclera 75, iris 71, and pupil 72 are clearly marked. Portions of iris 71 under eye lids 82U, 82L, although not seen, are shown for purposes of explaining the vision vector formulations. Iris 71 (and pupil 72) will almost always appear as an ellipse in these images. Only when operator 90 is looking directly at the emulator's video camera lens 12, will the shape of iris 71 (and pupil 72) approach that of a true circle. Iris 71 in image plane 40 corresponds to apparent iridal disc 64 in the model discussed previously in FIG. 4. Iris 71 has been modelled as a flat disc to simplify the algorithms which follow. Unless the operator's visual axes lie at angles greater than 35° to the z axis in the XYZ coordinate system defined above (FIG. 3), the iris in the image will appear as a well-defined, flat elliptic disc.

Figure 6:
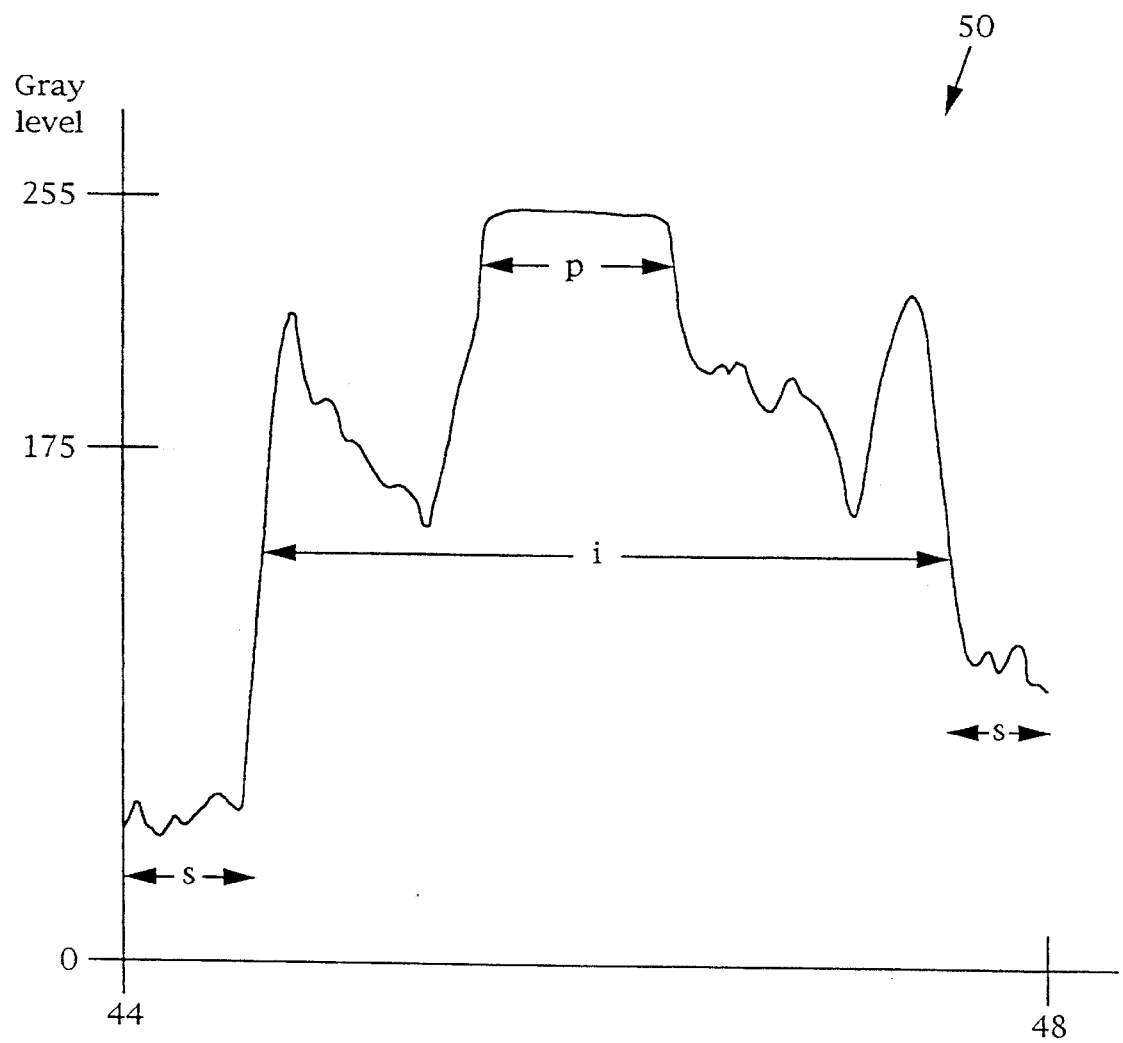
FIG. 6 is a plot of gray-scale values in an image scanning left to right across a human eye.

After eye 70, shown in FIG. 5, has been located in the image plane by image processor 20 using pattern recognition techniques well known in the art, the task of pinpointing the iridal boundary (between the iris and the sclera) begins. If the gray-scale values of pixels lying along the line shown between points 44 and 48 were plotted, the result would look something like the plot 50 of FIG. 6, which was taken from an actual gray-scale image of a human eye. The left scale is gray scale value; the bottom scale represents pixel positions on the line between points 44 and 48.

The sections of plot 50 representative of the sclera "s", the iris "i", and the pupil "p" are easily discernable. The variation in gray-levels between the outer edge of the iris and the pupil can be attributed to the "speckled" nature of the iris' coloring. The variation in mean gray-level between the scleral area near the left side 44 of plot 50 and the right 48 could be a result of shadowing by the eyelid and/or small differences in reflectance on the left and right sides of the iris. Notice that a relatively dark line of iridal color, as indicated by the two outside peaks, circumscribes the iris, and offers an excellent point of reference for the iridal boundary. Pixels nearest these peak values, or perhaps at points along the outer slope, e.g. at gray-level 175, can be selected algorithmically to represent the iridal boundary.

Returning to FIG. 5, the iridal boundary recognition algorithm extends this process along the iridal boundary as defined, taking care to avoid the secondary boundaries between the iris 71 and upper 82U and lower 82L eyelids, until a sufficient number of points 83 have been identified to determine the equation for an ellipse which most identically fits that of the iris 71 in the image, even in areas obscured by the operator's eyelids. Depending on the resolution required by a particular application, these points may be identified by single pixels, located in the image plane by their x and y distances from the origin (0,0). If greater resolution is required than can be supplied by the CCD sensor in the system, another algorithm can be constructed to find inter-pixel points which are closer to the thresholds (peak values or slope) established for the conditions encountered.

The elliptic function for the iridal boundary (as it appears in the image plane 40) is defined by five parameters: $x_{os}$, the x-offset, i.e., the x distance to the center of the iridal ellipse; $y_{os}$, the y-offset, the y distance to the center of the iridal ellipse; $a_e$, ½ the length of the major axis; $b_e$, ½ the length of the minor axis; and $\alpha$, the rotation angle of the ellipse with respect to the x axis. The distances are in pixels. All five parameters may be calculated from a least-squares fit of the general elliptic function to those boundary points 83 identified by the algorithm discussed above. These points are henceforth generically denoted by the couplet $(x_i,y_i)$. The general elliptic function is defined as:

$$\frac{[\sin\alpha(y_i - y_{os}) + \cos\alpha(x_i - x_{os})]^2}{b_e^2} + \frac{[\cos\alpha(y_i - y_{os}) - \sin\alpha(x_i - x_{os})]^2}{a_e^2} = 1 \quad \text{(Equation 1)}$$

When simplified, this equation fits the form:

$$Ax_i^2 + Bx_iy_i + Cy_i^2 + Dx_i + Ey_i + F = 0 \quad \text{(Equation 2)}$$

where: $B^2 - 4AC < 0$ For the least-squares fit, this equation may be recast in the form:

$$y_i^2 = A'x_i^2 + B'x_iy_i + D'x_i + E'y_i + F' \quad \text{(Equation set 3)}$$

where:

$$A' = \frac{-(b_e^2\sin^2\alpha + a_e^2\cos^2\alpha)}{a_e^2\sin^2\alpha + b_e^2\cos^2\alpha} = -A/C$$

$$B' = \frac{-[(a_e^2 - b_e^2)\sin 2\alpha]}{c} = -B/C$$

$$D' = \frac{2Ax_{os} + By_{os}}{c} = -D/C$$

$$E' = \frac{2Cy_{os} + Bx_{os}}{c} = -E/C$$

$$F' = \frac{a_e^2b_e^2 - Ax_{os}^2 - Bx_iy_i - Cy_{os}^2}{c} = -F/C$$

The five parameters defining the iridal ellipse can now be determined from a least-squares fit of the iridal boundary points to this function. Fifty to a hundred points, spread along the boundaries on both sides of the iris, will provide excellent precision to later algorithms.

From the list of boundary points $(x_i, y_i)$, the following list is calculated:

$\Sigma y_i^2 = a$ $\Sigma x_i^2 = b$ $\Sigma x_i y_i = c$ $\Sigma x_i = d$ $\Sigma y_i = e$ $\Sigma y_i^3 = f$ $\Sigma x_i^2 y_i = g$ $\Sigma x_i y_i^2 = h$ $\Sigma x_i^3 = m$ $\Sigma x_i y_i^3 = p$ $\Sigma x_i^3 y_i = r$ $\Sigma x_i^2 y_i^2 = s$ $\Sigma x_i^4 = t$ (Equation set 4)

and # of pixel points=n

For the least squares fit, the following five equations are required to solve for the five unknown coefficients, A', B', D', E', and F', from the general elliptic function:

$a = A'b + B'c + D'd + E'e + F'n$ $f = A'g + B'h + D'c + E'a + F'e$ $h = A'm + B'g + D'b + E'c + F'd$ $p = A'r + B's + D'g + E'h + F'c$ $s = A't + B'r + D'm + E'g + F'b$ (Equation set 5)

Solving this system of equations by elimination, the following lists of calculations are then performed:

$a' = fn - ae$ $b' = gn - be$ $c' = hn - ce$ $d' = cn - de$ $e' = an - e^2$ $f' = hn - ad$ $g' = mn - bd$ $h' = gn - cd$ $m' = bn - d^2$ $n' = pn - ac$ $p' = rn - bc$ $r' = sn - c^2$ $s' = sn - ab$ $t' = tn - b^2$ $a'' = e'f' - a'd'$ $b'' = e'g' - b'd'$ $c'' = e'h' - c'd'$ $d'' = e' + m' - d'^2$ $e'' = e'n' - a'c'$ $f'' = e'p' - b'c'$ $g'' = e'r' - c'^2$ $h'' = e's' - a'b'$ $m'' = e't' - b'^2$ $a''' = d''e'' - a''c''$ $b''' = d''f'' - c''^2$ $c''' = d''g'' - c''^2$ $d''' = d''h'' - a''b''$ $e''' = d''m'' - b''^2$ (Equation set 6)

Then, solving:

$A' = \dfrac{c'''d''' - a'''b'''}{c'''e''' - b'''^2}$ (Equation set 7)

$B' = \dfrac{a''' - A'b'''}{c'''}$ $D' = \dfrac{a'' - A'b'' - B'c''}{d''}$ $E' = \dfrac{a' - A'b' - B'c' - D'd'}{e'}$ $F' = \dfrac{a - A'b - B'c - D'd - E'e}{n}$ Finally, we may now substitute and solve for:

$2\alpha = \arctan[B'/(A'+1)]$ (Equation set 8)

$y_{os} = \dfrac{2A'E' - D'(A'+1)\tan 2\alpha}{4A' + (A'+1)^2 \tan^2 2\alpha}$ $x_{os} = \dfrac{(A'+1)y_{os}\tan 2\alpha + D'}{-2A'}$ $a_e^2 = \dfrac{(F' - A'x_{os}^2 + y_{os}^2)\cos 2\alpha - (A'+1)x_{os}y_{os}\sin 2\alpha}{A'\sin^2\alpha + \cos^2\alpha}$ $b_e^2 = \dfrac{-[(F' - A'x_{os}^2 + y_{os}^2)\cos 2\alpha - (A'+1)x_{os}y_{os}\sin 2\alpha]}{\sin^2\alpha + A'\cos^2\alpha}$ We now have the location and orientation of the iridal ellipse within the image in terms of measurable parameters.

In all, this process requires fewer than 700 multiply and divide instructions for each eye, and even a slow processor performing one multiply or divide per microsecond requires less than one millisecond of real-time to complete these calculations.

Once the five parameters have been calculated for the iridal ellipse, the location and orientation of the optical axis 79 can be determined. Optical axis 79 can be easily and precisely identified by a optical axis unit vector 79V pointing out from the center of the apparent iridal disc. To find this unit vector 79V, it is necessary to first calculate positions (in the referenced XYZ coordinate system) for at least three points on the iridal disc, including the center. Once these points are found, a simple cross-product of the vectors between the center of the disc and two other points on that disc will produce the unit vector 79V required.

Figures 7A, 7B:
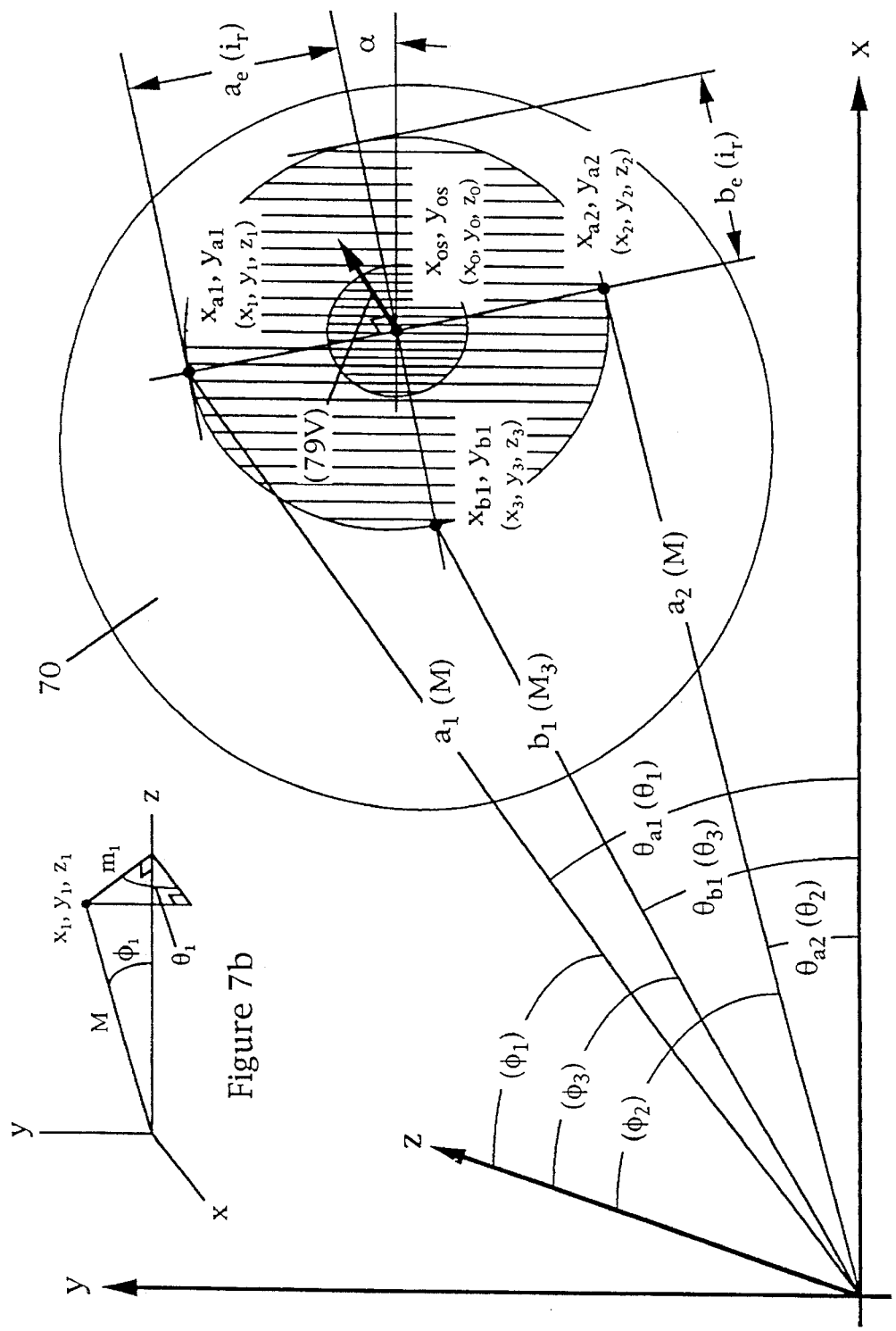

FIG. 7a illustrates left eyeball 70 (as it might appear magnified, and stripped of all surrounding tissue) in the virtual image plane 40 of the sensor 15 in the preferred embodiment. The Z axis has been added to serve as a reference to FIG. 7b. Note that four points, i.e. three on the edge of the apparent iridal disc and one at the center, have been identified. Each point has been denoted by a coordinate couplet and triplet, e.g. $(x_{os}, y_{os})$ and $(x_0, y_0, z_0)$. The couplet associates the point to the image plane; the triplet to the XYZ coordinate system defined by the sensor's optical system. (All symbols in FIG. 7a bounded by parentheses represent spatial values.) At this time, none of the triplets are known. The couplet $(x_{os}, y_{os})$ is known. The other three can be easily calculated from the five iridal parameters using trigonometry. For example, it can be seen that: $x_{a1}=x_{os}-a_e\sin\alpha$, and $y_{a1}=y_{os}+a_e\cos\alpha$. The distance in the image plane (in pixels) between the origin (0,0) and each point on the edge of the apparent iridal disc is simply the hypotenuse of the triangle formed by the point's x and y coordinates: $b_1=(x_{b1}^2+y_{b1}^2)^{1/2}$, for example.

Because the axes in the virtual image plane are placed as defined, i.e. coincident with the spatial x and y axes, and because the z axis is considered therefore to pass with some accuracy through a point at (or very close) to the center of the primary, light-gathering lens, any line in the image which passes through the origin represents not only a distance measured in pixels, but also a spatial angle, i.e. one which can be directly related to the field-of-view of the image sensor's optics by some function, $f_{op}$. All of the distances $a_1$, $a_2$, and $b_1$ in FIG. 7, therefore, also represent unique angles in the XYZ coordinate system of the preferred embodiment.

FIG. 7b helps clarify the physical relationships that exist between one of the spatial points identified with the iridal disc, $(x_1,y_1,z_1)$ in this case, and its corresponding point in the virtual image plane, $(x_{a1},y_{a1})$. FIG. 7b depicts point $(x_1,y_1,z_1)$ as located and measured in the image plane's attendant XYZ coordinate system. As shown, a right triangle can be constructed where hypotenuse M connects the origin in the inset diagram with the point $(x_1,y_1,z_1)$, and where side $m_1$ intersects the z axis at a distance $z_1$ from the origin (0,0,0). The projection of $m_1$ through the sensor's optics would produce line $a_1$ as it appears in the image plane. The spatial angle $\phi_1$ between M and the z axis is therefore related to $a_1$ by $f_{op}$, i.e. $\phi_1=f_{op}(a_1)$. Additionally: 1) the extended plane defined by this right triangle (M,$m_1$,Z axis) also contains line $a_1$, and 2) the xz plane in the XYZ coordinate system also contains the x axis shown in the image plane. Therefore, the spatial angle $\phi_1$ formed by the intersection of these two planes is also equal to the plane angle $\Theta_{a1}$ in the virtual image plane formed by the intersection of $a_1$ and the x axis. The lines $a_2$ and $b_1$ are related to angles $\phi_2$, $\Theta_2$, $\Theta_{a2}$ and $\phi_3$, $\Theta_3$, $\Theta_{b1}$ in a similar fashion.

The iridal disc in space is circular when viewed straight on, not elliptic as it most always appears when projected into the image plane. Interestingly, due to the nature of light and perspective, no matter what orientation the apparent iridal ellipse takes when viewed in the image, i.e. no matter how large or small the rotation angle, $\alpha$, the two points in space which correspond to the edge points of the major axis of the ellipse, e.g. $(x_{a1}y_{a1})$ and $(x_{a2},y_{a2})$, are equidistant from the origin, denoted as M in FIG. 7. Additionally, the distance in space between the two edge points, $(x_1y_1z_1)$ and $(x_2y_2,z_2)$, is equivalent to twice the iridal radius $i_r$. It is also clear from geometry, therefore, that:

$$(x_1-x_2)^2+(y_1-y_2)^2+(z_1-z_2)^2=(2i_r)^2 4i_r^2 \quad \text{(Equation 9)}$$

Further, each of the coordinates which define the two points can be expressed in terms of M, an unknown, and the two known angles associated with each of them—$\phi_1$ and $\Theta_{a1}$ for $a_1$; $\phi_2$ and $\Theta_{a2}$ for $a_2$—thus:

$$z_1=M\cos\phi_1$$
$$m_1=M\sin\phi_1$$
$$x_1=m_1\cos\Theta_{a1}=M\sin\phi_1\cos\Theta_{a1}$$
$$y_1=m_1\sin\Theta_{ai}=M\sin\phi_1\sin\Theta_{ai}$$

$$z_2=M\cos\phi_2$$
$$m_2=M\sin\phi_2$$
$$x_2=m_2\cos\Theta_{a2}=M\sin\phi_2\cos\Theta_{a2}$$
$$y_2=m_2\sin\Theta_{a2}=M\sin\phi_2\sin\Theta_{a2} \quad \text{(Equation set 10)}$$

Substituting these values into the previous equation (Equation 9) and simplifying gives:

$$(x_1-x_2)^2=M^2(\sin^2\phi_1\cos^2\Theta_{a1}-2\sin\phi_1\cos\Theta_{a1}\sin\phi_2\cos\Theta_{a2}+\sin^2\phi_2\cos^2\Theta_{a2})$$

$$(y_1-y_2)^2=M^2(\sin^2\phi_1\sin^2\Theta_{a1}-2\sin\phi_1\sin\Theta_{a1}\sin\phi_2\sin\Theta_{a2}+\sin^2\phi_2\sin^2\Theta_{a2})$$

$$(z_1-z_2)^2=M^2(\cos^2\phi_1-2\cos\phi_1\cos\phi_2+\cos^2\phi_2) \quad \text{(Equation set 11)}$$

From this, factoring out $M^2$, it is clear that:

$$M^2=4i^2r/(\sin^2\phi_1\cos^2\Theta_{a1}-2\sin\phi_1\cos\Theta_{a1}\sin\phi_2\cos\Theta_{a2}+\sin^2\phi_2\cos^2\Theta_{a2}+\sin^2\phi_1\sin^2\Theta_{a1}-2\sin\phi_1\sin\Theta_{a1}\sin\phi_2\sin\Theta_{a2}+\sin^2\phi_2\sin^2\Theta_{a2}+\cos^2\phi_1-2\cos\phi_1\cos\phi_2+\cos^2\phi_2) \quad \text{(Equation 12)}$$

If the iridal radius, $i_r$, for this particular operator is a value already known to the emulator software, then this value may be substituted into Equation 12 and the value of M can be calculated. If $i_r$ is not known, an estimated value, e.g. the value of the average human iridal radius, may be substituted to calculate M.

Once the value of M has been found, $(x_1,y_1,z_1)$ and $(x_2,y_2,z_2)$ may be calculated from the set of equations above, which expressed each coordinate in terms of M, $\phi_i$, and $\Theta_{ai}$. Subsequently, the coordinates of the center of the pupil or iris, $(x_0,y_0,z_0)$, can be calculated as follows:

$$x_0=(x_1-x_2)/2$$
$$y_0=(y_1-y_2)/2$$
$$z_0=(z_1-z_2)/2 \quad \text{(Equation set 13)}$$

In turn, $(x_3,y_3,z_3)$ can be similarly expressed in terms of $M_3$ (another unknown length), $\phi_3$, and $\Theta_{b1}$, and substituted into the expression:

$$(x_3-x_1)^2+(y_3-y_1)^2+(z_3-z_1)^2=2i_r^2 \quad \text{(Equation 14)}$$

where root(2)$i_r$ is equal to the spatial distance between $(x_1,y_1z_1)$ and $(x_3,y_3,z_3)$. From this, simplification produces the following equation:

$$2i_r^2=M_3^2(\sin^2\phi_3\cos^2\Theta_{b1}+\sin^2\phi_3\sin^2\Theta_{b1}+\cos^2\phi_3)+M_3(-2x_1\sin\phi_3\cos\Theta_{b1}-2y_1\sin\phi_3\sin\Theta_{b1}-2z_1\cos\phi_3)+x_1^2+y_1^2+z_1^2 \quad \text{(Equation 15)}$$

This is a quadratic equation of the form:

$$aM_3^2+bM_3+c=0, \text{ where}$$

$$a=(\sin^2\phi_3\cos^2\Theta_{b1}+\sin^2\phi_3\sin^2\Theta_{b1}+\cos^2\phi_3)$$

$$b=(-2x_1\sin\phi_3\cos\Theta_{b1}-2y_1\sin\phi_3\sin\Theta_{b1}-2z_1\cos\phi_3)$$

$$c=x_1^2+y_1^2+z_1^2-2i_r^2 \quad \text{(Equation set 16)}$$

Then, solving for $M_3$:

$$M_{3(1)}=[-b+(b^2-4ac)^{1/2}]/2a$$

$$M_{3(2)}=c/[aM_{3(1)}] \quad \text{(Equation set 17)}$$

The correct value, either $M_{3(1)}$ or $M_{3(1)}$, can be determined from the positional relationship between the coordinate points in the virtual image plane. Subsequently, as before, $(x_3,y_3,z_3)$ can be calculated from $M_3$, $\phi_3$, and $\Theta_{b1}$. Finally, a cross-product of the two vectors defined by $(x_0,y_0,z_0)\&(x_1,y_1,z_1)$ and $(x_0,y_0,z_0)\&(x_3,y_3,z_3)$ will produce the unit vector 69V,79V which inherently expresses the instantaneous optical axis of that particular eye.

The Point-of-gaze

With that, the point-of-gaze calculation is essentially complete. An estimate of just one variable must be supplied to the critical algorithms, that of the iridal radius, $i_r$. During initialization, a value generally accepted as the average "apparent" iridal radius, e.g. 6 millimeters, can be used. The vectors then calculated and representing the operator's two optical axes 69,79 may be extended (toward monitor screen 37 in the preferred embodiment) to any length. During a calibration procedure following initialization, operator 90 can be asked to focus sequentially upon a series of points highlighted on monitor screen 37. From this process, a biasing function may be developed for each optical axis which provides enough precision over a wide enough range of motion to meet the needs of the application at hand. (In fact, other applications certainly exist where line-of-sight is the crucial factor. In these cases, the optical axis unit vector 69V or 79V, and biasing function for a single eye could provide all the information required.)

If greater precision in the point-of-gaze calculation is necessary, improved estimates of the operator's actual iridal radii may be folded into the biasing functions being developed over the course of the calibration procedure. If maximum precision is needed for a particular application, the unit vectors 69V,79V for the optical axes 69,79 can be converted to the unit vectors which represent the visual axes 63,73. This can be accomplished by constructing two planes. The first is defined by the two points at either end of the unit vector for the left eye and the source point of the unit vector for the right eye, and the second by the two points at either end of the unit vector for the right eye and the source point of the unit vector for the left eye. (All things considered, although the model defined in FIG. 4 indicates that all four vision vectors lie in the same plane, experience suggests some error, however small, will always prevent practical realization of this model.) Rotating the first vision vector in the first plane inboard, toward the other eye, through angle $\alpha_f$ as shown in FIG. 4, and the second vision vector in the second plane inboard, through the same angle results in vectors that are along the operator's two visual axes 63,73. Improved estimates of angle $\alpha_f$ for any particular operator also may be folded into the biasing functions being developed over the course of the calibration procedure.

Brief Description of Another Potential Application

This point-of-gaze measurement methodology can be used in a variety of applications where a precise estimate of any operator's three dimensional point-of-gaze (or even mere line-of-sight) is required. For instance, stereoscopic vision goggles may give the impression of three dimensions, but the human vision processor in the brain relies on other cues not present in a static stereoscopic scene. One of these clues may be a certain fuzziness in a real scene outside the area around the viewer's point-of-gaze. A stereoscopic vision system, therefore, for this reason alone, may find information about the user's point-of-gaze essential, as it is then able to process individual scenes and present them to the operator in a way that more nearly mimics three dimensional viewing.

Inside the goggles that are needed for this application, however, it may not be possible to gather enough light from the sensors viewing the operator's eyes to operate passively (as with the preferred embodiment). Other light sources, such as infrared sources collimated to each sensor's optical axis, may be required. In this case, of course, filters will prevent all but infrared radiation from entering the sensors, which radiation, when properly gathered, will consist solely of that being reflected (from the user's retina) out of the operator's pupils. Because the sensors are in this instance not only fixed to the display scene but to the operator as well, the fact that the operator's pupils are not fixed in size (unlike the iris) becomes unimportant. The method described in this document will still operate in a similar manner. The five parameters for the pupillary ellipse will be calculated exactly as are the iridal ellipse parameters; the only difference being the pre-calibration value inserted for the pupillary diameter. From there, the calculation of the optical and (if necessary) visual axes will proceed identically. When the calibration is complete the algorithms will have similarly developed a precise estimate of the pupillary diameter. Subsequently, because the sensors' positions are fixed with respect to the operator's eyes, any changes in the size of those diameters (as manifested by changes in the size of the pupillary diameter) can be attributed to dilation (or its opposite) as the ambient light the eyes are exposed to changes over time.

Because this point-of-gaze methodology is widely applicable, claims for the patent ignore application specific details. Additionally, the algorithms detailed herein, which calculate the five iridal parameters and the optical axis unit vector(s), are not intended to illustrate the only possible way of performing these calculations. For instance, either calculation, in part or all, might possibly be designed into a single application specific integrated circuit (ASIC), where only the inputs (points in the plane) and outputs (five parameters or optical axis unit vectors) could reveal the path traversed. Similarly, it is possible, using $e_r$ and $i_r$ as variables (along with the five parameters), to find the center point of the eyeball and the center point of the iridal disc instead of three points in the plane of the iridal disc. Obviously, these two points also define a vector which is equivalent to the optical axis in question. For these reasons, the claims for the Point-of-gaze Measurement Methodology are concerned with the general algorithmic path rather than the specific calculations detailed in this document.

Although a particular embodiment of the invention has been illustrated and described, various changes may be made in the form, composition, construction, and arrangement of the parts without sacrificing any of its advantages. Therefore, it is to be understood that all matter herein is to be interpreted as illustrative and not in any limiting sense, and it is intended to cover in the appended claims such modifications as come within the true spirit and scope of the invention.

In the following claims the word ellipse includes the special case of a circle.

I claim:

1. A device for determining, relative to a camera, an optical axis vector of an operator; said device comprising:

a camera oriented so as to observe at least a portion of the iridal-scleral boundary of an eye of an operator; said camera for obtaining an image of at least a portion of the iridal-scleral boundary of the eye of the operator; and a computer with memory including:
analyzing means for analyzing the obtained image and for locating therein a plurality of points on the iridal-scleral boundary;
determining means for determining, from the plurality of located points on the iridal-scleral boundary, the size and position of the iridal ellipse in the image; and formulating means for formulating, using the determined ellipse, the optical axis vector for the eye relative to said camera.

2. The device of claim 1:

said formulating means using a predetermined value for the radius of the iris of the eye of the operator in formulating the optical axis vector.

3. The device of claim 1:

the spatial location of the eye of the operator relative to the camera being originally unknown.

4. The device of claim 1:

the spatial location of the eye of the operator relative to the camera being originally unknown; and said formulating means using the determined iridal ellipse and a predetermined value for the radius of the iris of the eye of the operator in formulating the optical axis vector.

5. The device of claim 1 including:

digitizing means for digitizing the image obtained by said camera; and said analyzing means includes means for analyzing the digitized image for locating therein a plurality of points on the iridal-scleral boundary as represented by different light intensities.

6. The device of claim 5:

said formulating means using a predetermined value for the radius of the iris of the eye in formulating the optical axis vector.

7. A device for determining, relative to a camera, an optical axis vector for an eye of an operator, said device comprising:

a camera located at a known spatial position relative to the eye of the operator and oriented so as to observe at least a portion of the pupillary boundary of the eye; said camera for obtaining an image of at least a portion of the pupillary boundary of the eye of the operator; and a computer with memory including:

analyzing means for analyzing the obtained image and for locating therein a plurality of points on the pupillary boundary;

determining means for determining, from the plurality of located points on the pupillary boundary, the size and position of the pupillary ellipse in the image; and formulating means for formulating, using the determined ellipse, an optical axis vector for the eye relative to said camera.

8. A method for determining, relative to a camera, an optical axis vector for an eye of an operator; said method comprising the steps of:

obtaining, with a camera, an image of at least a portion of the iridal-scleral boundary of the eye of the operator;

analyzing the obtained image to locate therein a plurality of points on the iridal-scleral boundary;

determining, from the located points, the size and position of the iridal ellipse in the image; and formulating, by using the determined iridal ellipse, an optical axis vector for the eye relative to the camera.

9. The method of claim 8 wherein the step of formulating the optical axis vector uses a predetermined value for the radius of the iris of the eye of the operator.

10. The method of claim 8 wherein the step of formulating the optical axis vector uses only the determined iridal ellipse and a predetermined value for the radius of the iris of the eye of the operator in formulating the optical axis vector.

11. The method of claim 8 wherein:

the spatial location of the eye of the operator relative to the camera is originally unknown.

12. The method of claim 8 wherein:

the step of formulating the optical axis vector uses only the determined iridal ellipse and a predetermined value for the radius of the iris of the eye of the operator in formulating the optical axis vector; and the spatial location of the eye of the operator relative to the camera is originally unknown.

13. A method for determining, relative to a camera, an optical axis vector for an eye of an operator; said method comprising the steps of:

obtaining, with a camera, a digitized image of at least a portion of the iridal-scleral boundary of the eye of the operator;

analyzing the digitized image to locate therein a plurality of points on the iridal-scleral boundary as represented by different light intensities;

determining, from the located points, the size and position of the iridal ellipse in the image; and formulating, by using the determined iridal ellipse, an optical axis vector for the eye relative to the camera.

14. The method of claim 13 wherein the step of formulating the optical axis vector uses a predetermined value for the radius of the iris of the eye of the operator.

15. The method of claim 13 wherein the step of formulating the optical axis vector uses only the determined iridal ellipse and a predetermined value for the radius of the iris of the eye of the operator in formulating the optical axis vector.

16. The method of claim 13 wherein:

the spatial location of the eye of the operator relative to the camera is originally unknown.

17. The method of claim 13 wherein:

the step of formulating the optical axis vector uses only the determined iridal ellipse and a predetermined value for the radius of the iris of the eye of the operator in formulating the optical axis vector; and the spatial location of the eye of the operator relative to the camera is originally unknown.

\* \* \* \* \*